United States Patent
Giannini et al.

(10) Patent No.: US 7,572,778 B2
(45) Date of Patent: Aug. 11, 2009

(54) FLUOROCOMBRETASTATIN AND DERIVATIVES THEREOF

(75) Inventors: Giuseppe Giannini, Pomezia (IT); Domenico Alloatti, Rome (IT); Marcella Marcellini, Rome (IT); Mauro Marzi, Rome (IT); Teresa Riccioni, Rome (IT); Maria Ornella Tinti, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 377 days.

(21) Appl. No.: 10/563,480

(22) PCT Filed: Jul. 6, 2004

(86) PCT No.: PCT/IT2004/000375
§ 371 (c)(1),
(2), (4) Date: Jan. 5, 2006

(87) PCT Pub. No.: WO2005/007603
PCT Pub. Date: Jan. 27, 2005

(65) Prior Publication Data
US 2006/0160778 A1 Jul. 20, 2006

(30) Foreign Application Priority Data
Jul. 18, 2003 (GB) .................................. 0316910.9

(51) Int. Cl.
*A61K 31/66* (2006.01)
*C07F 9/02* (2006.01)

(52) U.S. Cl. ...................................... 514/130; 558/194
(58) Field of Classification Search .............. 558/194; 514/130
See application file for complete search history.

(56) References Cited

FOREIGN PATENT DOCUMENTS

EP 0 731 085 A 9/1996
WO 02/5007 A 6/2002

OTHER PUBLICATIONS

Lawrence et al., 2003, CAS: 138:385212.*
Tsai's. 1996, CAS: 124:231924.*
International Search Report of PCT/IT2004/000375, mailed Apr. 1, 2005.
J. Med. Chem., vol. 35, No. 12, 1992, pp. 2293-2306.
Database Beilstein, Beilstein Institute for Oragnic Chemistry, XP002312832, retrieved from XFIRE, Database accession No. 7965335.
J. Nat. Prod., vol. 63, No. 7, 2000, pp. 969-974.
Bioorg. Med. Chem. Lett., vol. 8, No. 23, 1998, pp. 3371-3374.
J. Med. Chem., vol. 46, No. 16, 2003, pp. 3546-3554.
Bull. Chem. Soc. Jpn., vol. 71, No. 12, 1998, pp. 2903-2922.
Helv. Chim. Acta., vol. 82, No. 12, 1999, pp. 2231-2239.
Hou-Jen Tsai, "Synthesis of Phenyl Substituted Fluoro-Olefins", Tetrahedron Letters, vol. 37, No. 5, 1996, pp. 629-632, XP002312830.
J. Heterocycl. Chem., vol. 3, 1996, pp. 247-251.
Chem. Pharm. Bull., vol. 40, No. 10, 1992, pp. 2842-2844.
Griggs et al, "Inhibition of Proliferative Retinopathy . . . ", American Journal of Pathology, vol. 160, No. 3, Mar. 2002.
Cirla et al, "Combretastatins: from natural products to drug discovery", Nat. Prod. Rep., 2003, 20, 558-564.
Nambu et al, "Combretastatin A-4 Phosphate Suppresses Development . . . ", Investigative Ophthalmology & Visual Science, Aug. 2003, vol. 44, No. 8.
Nabha et al, "Combretastatin A-4 Prodrug Induces Mitotic . . . ", Clinical Cancer Research, vol. 8, 2735-2741, Aug. 2002.
Griggs et al, "Combretastatin-A4 Disrupts Neovascular Development . . . ", British Journal of Cancer (2001) 84(6), 832-835.
Nabha et al, "Preclinical Report Evaluation of Combretastatin A-4 prodrug in a non-Hodgkin's . . . ", Anti-Cancer Drugs, 2001, 12, pp. 57-63.
Pinney et al, "Synthesis and Biological Evaluation of Aryl Azide Derivatives of Combretastatin A-4 . . . ", Bioorganic & Medicinal Chemistry 8 (2000) 2417-2425.

* cited by examiner

*Primary Examiner*—Rei-tsang Shiao
(74) *Attorney, Agent, or Firm*—Nixon & Vanderhye P.C.

(57) ABSTRACT

The present invention is related to new derivatives of Combretastatin, of Formula

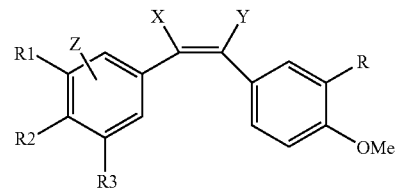

obtained by total synthesis. The strategy developed for each of the compounds is to i) replace a halogen (i.e. fluorine atom) to hydrogen on olefinic bound; ii) replace an aromatic ring in a natural product with an amino-aromatic ring. Said compounds recognize and bind the tubulin site: are useful for treating pathological states which arise from or are exacerbated by cell proliferation—as anticancer and/or antiangiogenic activity, in a mammal—to pharmaceutical compositions comprising these compounds.

15 Claims, 6 Drawing Sheets

FIGURE 1

Scheme 1: synthesis of difluorocombretastatin

FIGURE 2

Scheme 2: Synthesis of difluoro-Nitro- and difluoro-Amino-combretastatin

Overall yield = 3 %

FIGURE 3

Scheme 3: Synthesis of monofluorocombretastatins

Scheme 3a: Total synthesis approach to monofluorocombretastatin

W = $NO_2$, OH, OTBDMS

FIGURE 4

Scheme 4: Synthesis of disodium-phosphate prodrug difluorocombretastatin (ST2493)

FIGURE 5

Scheme 5: Synthesis of disodium mono-difluorocombretastatin-4-O-methyloxyphosphate [12]

FIGURE 6

Scheme 6: General Procedure for obtaining amide derivatives [13].

FIGURE 7

Scheme 7: Synthesis of bromofluorocombretastatin

FLUOROCOMBRETASTATIN AND DERIVATIVES THEREOF

This application is the US national phase of international application PCT/IT2004/000375, filed 6 Jul. 2004, which designated the U.S. and claims priority of GB 0316910.9, filed 18 Jul. 2003, the entire contents of each of which are hereby incorporated by reference.

BACKGROUND OF THE INVENTION

Neoplastic diseases, characterized by the proliferation of cells which are not subject to normal cell proliferating controls, are a major cause of death in humans and other mammals. Cancer chemotherapy has provided new and more effective drugs to treat these diseases and has also demonstrated that drugs which disrupt microtubule synthesis are effective in inhibiting the proliferation of neoplastic cells.

Microtubules play a key role in the regulation of cell architecture, metabolism and division. The microtubule systems of eukaryotic cells comprises a dynamic assembly and disassembly matrix in which heterodimers of tubulin polymerize to form microtubules in both normal and neoplastic cells. Within neoplastic cells, tubulin is polymerized into microtubules which form the mitotic spindle. The microtubules are then depolimerized when the mitotic spindle's use has been fulfilled. Agents which disrupt the polymerization or depolymerization of microtubules in neoplastic cells, thereby inhibiting the proliferation of these cells, comprise some of the most effective cancer chemotherapeutic agents in use.

Combretastatin A-4 (CA-4), isolated from the African bush willow, Combretum caffrum (Combretaceae) (Pettit, G. R., et al.; *Experientia*, 1989, 45, 209) shows exciting potential as an anticancer agent binding strongly to tubulin at a site shared with, or close to, the colchicine binding site (Lin, C. N., et al; *Biochemistry*, 1989, 28, 6984). The bond to tubulin prevents its polymerization into microtubules with anti-mitotic effect. CA-4 inhibits cell growth at as low as nanomolar concentrations and shares many structural features common to other tubulin-binding agents such as colchicine and podophyllotoxin.

The phosphate salt [CA-4P] (Pettit, G. R., et al.; *Anticancer Drug Des.*, 1995, 10, 299), which has better water solubility than CA-4, has entered Phase II clinical trials.

It is the ability of combretastatins to damage tumor vasculature, thereby effectively starving tumors of nutrients, which makes them such exciting molecules.

Recently many studies have shown that a number of antiangiogenic agents, like CA-4P, can inhibit retinal neovascularization in a well-characterized murine model of ischemia-induced proliferative retinopathy.

These studies suggest that as CA-4P or new derivatives as other antiangiogenic agents, could be useful in the treatment of non-neoplastic diseases like ischemia-induced proliferative retinopathy (Griggs, J., et al., *Am. J. Pathol.*, 2002, 160 (3), 1097-103).

The spatial relationship between the two aromatic rings of combretastatin, colchicine and similar drugs is an important structural feature that determines their ability to bind to tubulin (McGown, A. T., et al., a) *Bioorg. Med. Chem. Lett.*, 1988, 8(9), 1051-6; b) *Bioorg. Med. Chem. Lett.*, 2001, 11(1), 51-4).

Since '80s researchers have discovered that the selective introduction of fluorine into biologically active molecules exerts an influence on activity. Therefore, important endeavour in drug design has been described and a number of compounds incorporating fluorine as a bioisosteric replacement for hydrogen were reported (Giannini, G., *Current Medicinal Chemistry*, 2002, 9, 687-712).

SUMMARY OF THE INVENTION

It has now been found that without any modification of the cis-stilbene motif the introduction of the strongly electron-withdrawing fluorine atom in olefin bond allows the biological activity to increase or, in case of the same activity, to influence the pharmacodynamics activity.

Fluoro and bromofluoro stilbenes have been synthesized.

Accordingly, it is an object of the present invention a compound of formula (I)

wherein:
$R_1$, $R_2$ and $R_3$, which can be the same or different, are H, OMe, $NO_2$, NHR';
Z=H or halogen
X and Y are halogen or H with at least one of them being halogen;
R=OH, $OPO_3Na_2$, $OCH_2OPO_3Na_2$, $NO_2$, NHR';
R'=H, alkyl ($C_1$-$C_6$), $(COCHR"NH)_n$—H;
R"=H, an amino acid side chain, Ph;
n an integer comprised between 1 and 3;
their pharmaceutically acceptable salts, racemates and single enantiomers.

Other objects of the present invention are processes for the preparation of the compounds of the above Formula (I).

Another object of the present invention is the use of the compounds of Formula (I) as test compounds in a biological assay for microtubule polymerization.

The compounds of Formula (I) have antitubulin activity at least comparable to that of CA-4 (*J. Med. Chem*, 2002, 45:1697-1711).

Another object of the present invention is the use of the compounds of Formula (I) as medicaments, in particular for the preparation of a medicament for treating pathological states which arise from or are exacerbated by cell proliferation.

A further object of the present invention are pharmaceutical compositions comprising at least a compound of Formula (I) as active ingredient in admixture with at least one pharmaceutically acceptable carrier and/or excipient.

These and other objects of the present invention shall be illustrated in detail also my means of Examples and Drawings, wherein, in the latter.

It shall be understood by the skilled person that in the FIGS. 1-7 synthetic schemes are provided for the preferred compounds of the present invention, but the skilled reader will understand that these schemes are applicable to the whole range of the invention, just selecting the appropriate starting materials, depending on the meanings in Formula (I), and resorting to the general common knowledge for the obvious modifications of the reaction conditions and reactants.

DETAILED DESCRIPTION OF THE INVENTION

According to the present invention, halogen means fluoro, chloro and bromo.

According to the present invention, R" is preferably the side chain of a natural amino acid, and in particular Ala, Asn, Asp, Cys, Gly, Gln, Glu, His, Ile, Leu, Lys, Met, Phe, Pro, Ser, Thr, Tyr, Try, Val.

Particularly preferred compounds are those of formula (I) wherein:

at least one of X and Y is halogen, $R_1$-$R_3$ are methoxy, and R is hydroxy;

at least one of X and Y is halogen, $R_1$-$R_3$ are methoxy, R is amino or substituted amino;

at least one of X and Y is halogen, $R_1$-$R_3$ are different from methoxy, R is hydroxy;

Z is hydrogen or halogen;

R is $OPO_3Na_2$ or $OCH_2OPO_3Na_2$;

R' is $(COCHR"NH)_n$—H.

Particularly preferred compounds are those wherein:

X=Y=F; R=$OPO_3Na_2$: difluorocombretastatin;
X=Y=F; R=$NH_2$: difluoroaminocombretastatin;
X=H; Y=F; R=$OPO_3Na_2$: monofluorocombretastatin;
X=F; Y=H; R=$OPO_3Na_2$: monofluorocombretastatin;
X=H; Y=F; R=$NH_2$: monofluoroaminocombretastatin;
X=F; Y=H; R=$NH_2$: monofluoroaminocombretastatin.
X=Br; Y=F; R=$OPO_3Na_2$ bromofluorocombretastatin Processes for the preparation of the compounds of the present invention shall be described in details, by making reference to the synthetic schemes appended as Figures.

The compounds of the present invention can be prepared by conventional synthetic methods, however, in some preferred embodiments of the present invention, the starting compound is a compound of formula (I), wherein both X and Y are hydrogen.

A process for the preparation of compounds of Formula (I), wherein X and Y are both F comprises the following steps:

a) reaction of 1-bromo-1,2-difluoro-2-(4-methoxy-3-(protected OH)-phenyl)ethene with 3-$R_1$-4-$R_2$-5-$R_3$-phenyl-boronic acid, and b) restoring the 3-(protected OH) group.

For step a), 1-bromo-1,2-difluoro-2-(4-methoxy-3-(protected OH)-phenyl)ethene can be obtained by synthetic methods available in the art. For example, isovanillin, with OH group suitably protected, is transformed into 1-bromo-1,2-difluoro-2-(4-methoxy-3-(protected OH)-phenyl)ethene.

Isovanillin is a commercially available product, as well as the 3,4,5-trisubstituted-phenyl-boronic acid is commercially available, or can be obtained by conventional methods. Also many other mono-, di-, and tri-substituted-phenyl-boronic acids are commercially available. However, the starting materials can be obtained by conventional methods.

Reaction of step a) is carried out in a suitable reaction medium, for example an organic solvent, or a mixture of water and the solvent, in the presence of aqueous base, for example an alkaline carbonate. The use of a catalyst can be advisable, and a preferred example is $Pd(Ph_3P)_4$. The reaction temperature is selected according to the starting materials, the solvent and the catalyst used. Preferably, the reaction temperature is at the reflux temperature of the reaction medium.

Removal of the protecting moiety from the hydroxy group is absolutely conventional and is normally performed by the person skilled in the art. A preferred protecting group is found among commercially available organosilyloxy derivatives, for example tert-butyl-dimethyl-syliloxyphenyl. Removal of such groups is done with conventional methods.

A process for the preparation of compounds of Formula (I), wherein one of the X and Y is F and the other one is hydrogen, comprises the following steps:

a) bromofluorination of the compound of Formula (I), wherein X and Y are H, and b) base-promoted HBr elimination.

This process is disclosed in Giannini, G., *Gazz. Chim. It.,* 1997, 127, 545; Thakker D. R., et al., *J. Org. Chem.,* 1989, 54, 3091.

Compounds of Formula (I), wherein one of the X and Y is F can be also prepared by a process comprising the following steps:

a) transformation of compound of Formula (I), wherein X and Y are H into the respective bromohydrin, and b) base-promoted HBr elimination.

This process is disclosed in Giannini, G., *Gazz. Chim. It.,* 1997, 127, 545; Thakker D. R., et al., *J. Org. Chem.,* 1989, 54, 3091.

In alternative, compounds of Formula (I), wherein one of the X and Y is F can be prepared by a process comprising the following steps:

a) transformation of compound of Formula (I), wherein X and Y are H into the respective epoxide;

b) epoxide opening to give the respective bromohydrin, and c) base-promoted HBr elimination, or in alternative, d) epoxide opening to give the respective fluorohydrin, and e) elimination of the opportune hydroxyl derivative.

This process is disclosed in Giannini, G., *Gazz. Chim. It.,* 1997, 127, 545; Thakker D. R., et al., *J. Org. Chem.,* 1989, 54, 3091.

Compounds of Formula (I), wherein one of the X or Y is F and the other is Br are prepared by a process comprising the following steps:

a) transformation of compound of Formula (I), wherein X and Y are H into the respective bromohydrin, and b) base-promoted HBr elimination.

This process is disclosed in Giannini, G., *Gazz. Chim. It.,* 1997, 127, 545; Thakker D. R., et al., *J. Org. Chem.,* 1989, 54, 3091.

In a preferred embodiment, the starting compound is Combretastatin A (Formula I, $R_1$, $R_2$, $R_3$=OMe, X and Y=H, R=OH).

In alternative, the monofluorocombretastatin derivatives, wherein one of the X or Y is F, can be prepared by a total synthesis.

Figure 7:
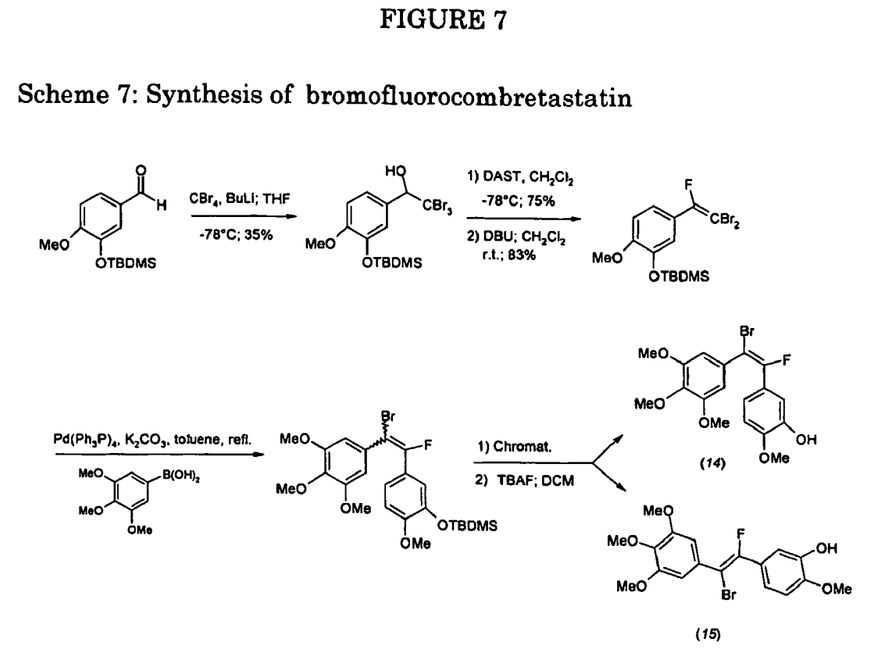
FIG. 7: synthesis of bromofluorocombretastatin

A process for the preparation of compounds of Formula (I), wherein X is Br and Y is F, is disclosed in Scheme 7.

Pharmaceutically acceptable salts are obtained with conventional methods reported in the literature and do not require any further description.

As above disclosed, the compounds of the present invention are useful as medicaments, and, due to their activity on tubulin site, they can be used for the preparation of a medicament for the treatment of pathological states which arise from or are exacerbated by cell proliferation.

An example of said pathological state is a tumour, and among them, both solid and haematic tumors can be treated, for example sarcoma, carcinoma, carcinoid, bone tumour, neuroendocrine tumour, lymphoid leukaemia, acute promyelocytic leukaemia, myeloid leukaemia, monocytic leukaemia, megakaryoblastic leukaemia and Hodgkin's disease.

In another aspect according to the present invention, said medicament is used for treating a pathological state caused by abnormal angiogenesis, such as, for example, tumour metastases; arthritic disease; diabetic retinopathy; psoriasis; chronic inflammatory diseases or arteriosclerosis.

In a further embodiment of the present invention, said medicament is used for treating a non-neoplastic disease, such as for example ischemia-induced proliferative retinopathy.

The pharmaceutical compositions will contain at least one compound of Formula (I) as an active ingredient, in an amount such as to produce a significant therapeutic effect. The compositions covered by the present invention are entirely conventional and are obtained with methods which are common practice in the pharmaceutical industry, such as, for example, those illustrated in *Remington's Pharmaceutical Science Handbook, Mack Pub. N.Y.*—latest edition. According to the administration route chosen, the compositions will be in solid or liquid form, suitable for oral, parenteral or intravenous administration. The compositions according to the present invention contain, along with the active ingredient, at least one pharmaceutically acceptable vehicle or excipient. These may be particularly useful formulation coadjuvants, e.g. solubilising agents, dispersing agents, suspension agents, and emulsifying agents.

The present invention shall now be further illustrated by means of Examples.

General Remarks: $^1$H— and $^{13}$C-NMR spectra were recorded in CDCl$_3$ solution as indicated, at 200 or 300 MHz, respectively. The chemical shift values are given in ppm and the coupling constants in Hz. Optical rotation data were obtained with a Perkin-Elmer model 241 polarimeter. Thin-layer chromatography (TLC) was carried out using Merck precoated silica gel F-254 plates. Flash chromatography was carried out using Macherey-Nagel silica gel 60, 230-400 mesh. Solvents were dried according to standard procedures, and reactions requiring anhydrous conditions were performed under nitrogen. Solutions containing the final products were dried with Na$_2$SO$_4$, filtered, and concentrated under reduced pressure using a rotatory evaporator.

Same abbreviation used in the experimental part: TBDM-SiCl (tert-butyldimethylchlorosilane); Hex (Hexane); DAST (Diethylaminosulfur trifluoride); DIPEA (diisopropylethylamine); PyBroP (Bromo-tris-pyrrolidino-phosphonium-hexafluoro-phospate); TAEA (tris(2-aminoethyl)amine).

EXAMPLE 1

Figure 1:
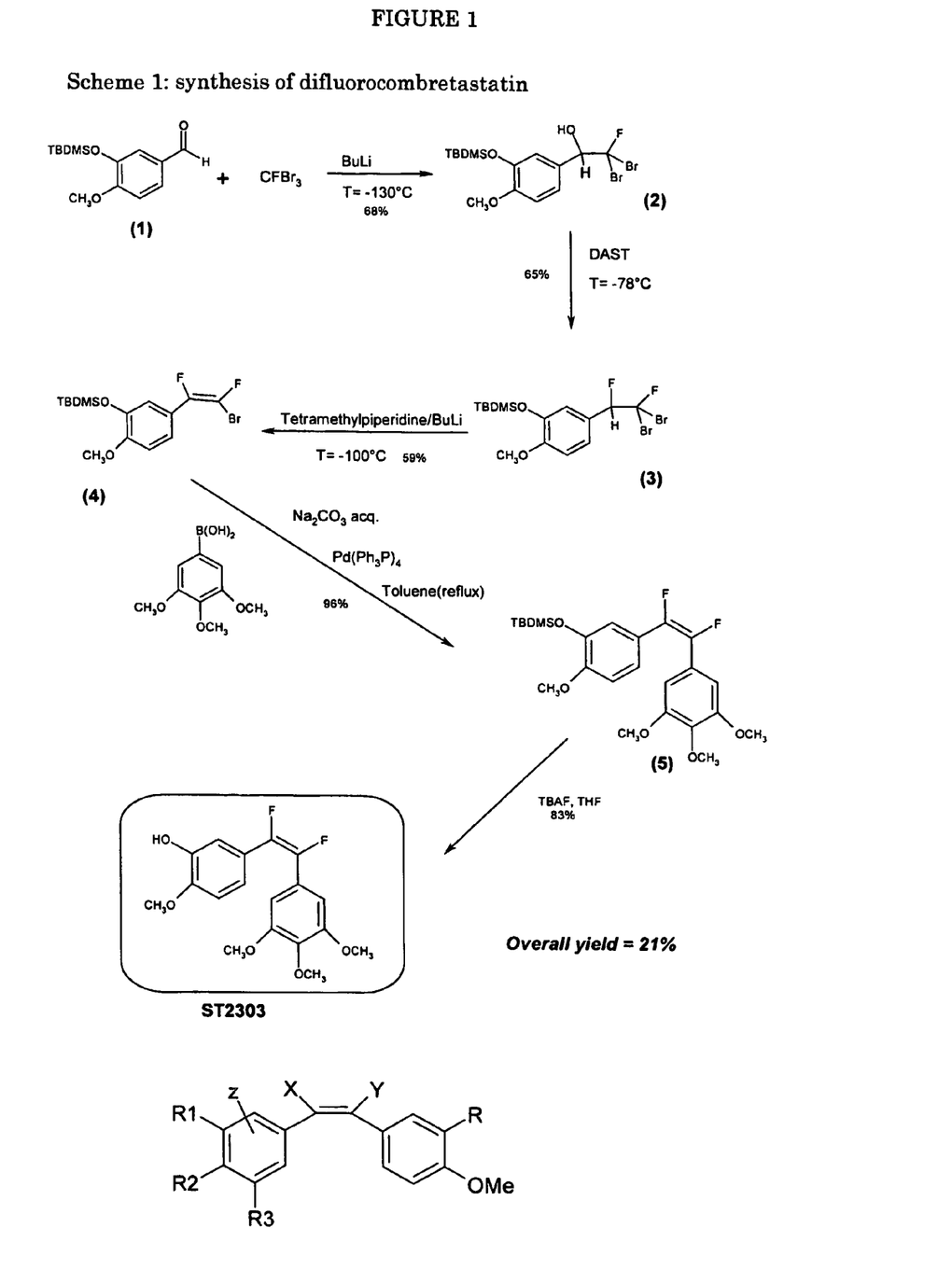
FIG. 1: synthesis of difluorocombretastatin.

Synthesis of difluorocombretastatin (Scheme 1)

Synthesis of tert-butyl-dimethyl-sylil isovanillin (1)

To a solution of 6.09 g (40 mmol) of Isovanillin in 50 mL of CH$_2$Cl$_2$, were added 6.64 g of TBDMSiCl (44 mmol, 1.1 eq.) and 2.95 g (44 mmol, 1.1 eq) of Imidazole. The solution was stirred at room temperature for three hours and then washed with 0.5 M HCl. The crude product was purified on a silica gel column using Hexane/Ethyl Acetate 9:1, to give 9 g (33 mmol, 83%) of a colourless oil. Rf=0.27 (Hex./Ethyl Acetate 95:5)

MS (IS): [MH]$^+$=267.2 [M+Na]$^+$=289.2 (main peak) $^1$H NMR (300 MHz, CDCl$_3$, δ): 0.2 (s, 6H, 2×CH$_3$), 1.0 (s, 9H, tBu), 3.9 (s, 3H, OCH$_3$), 6.9-6.95 (d, 1H, CH), 7.4 (s, 1H, CH), 7.45-7.5 (d, 1H, CH), 9.8 (s, 1H, CHO). $^{13}$C NMR (75 MHz, CDCl$_3$, δ): −4.4; 18.6; 25.9; 55.6; 111.9; 120.0; 126.5; 130.0; 146.0; 157.1; 191.0.

Synthesis of 2,2-dibromo-2-fluoro-1-(4-methoxy-3-tert-butyl-dimethyl-syliloxyphenyl)ethanol (2)

A mixture of 2.66 g (10 mmol) of TBDMS-Isovanillin and 2.98 g (11 mmol, 1.1 eq) of CFBr$_3$ in 80 mL of Et$_2$O/THF (1:1) was brought to T=−130° C.; 4.4 mL (11 mmol, 1.1 eq) of a 2.5 M BuLi solution in hexane was added to the mixture in 10 minutes. After two hours at T=−70° C., it was necessary to add 1.3 mL of BuLi solution and 0.3 mL of CFBr$_3$ to drive the reaction to completion.

The reaction was quenched with 60 mL of NH$_4$Cl saturated solution and diluted with 20 mL of diethyl ether. The aqueous phase was back-extracted with 2×20 mL of diethyl ether, the organic fractions were collected and dried over anhydrous sodium sulfate and then purified on a silica gel column using Hexane/Ethyl Acetate 95:5 to give 3.1 g (6.8 mmol, 68%) of a waxy solid. Rf=0.5 (Hex./AcOEt 85:15).

MS (IS): [M+Na]$^+$=479.1; 481.1; 483.1 (1:2:1) [M−1]−= 457.2 $^1$H-NMR (300 MHz, CDCl$_3$, δ): 0.2 (s, 6H, 2×CH$_3$), 1.0 (s, 9H, tBu), 3.8 (s, 3H, OCH$_3$), 5.0 (d, 1H, CH, 3JHF=10 Hz), 6.8-6.9 (d, 1H, CH$_{ar}$), 7.0-7.1 (t, 2H, 2×CH). $^{13}$C-NMR (75 MHz, CDCl$_3$, δ): 4.4; 18.6; 25.9; 55.6; 82.7; 83.0; 101.3; 105.6; 111.5; 121.3; 122.2; 127.5; 144.9; 152.2.

Synthesis of 1,1-dibromo-1,2-difluoro-2-(4-methoxy-3-tert-butyl-dimethyl-syliloxyphenyl)ethane (3)

(Diethylamino)sulfur trifluoride 1.5 mL (11.2 mmol; 1.8 eq) in 10 mL CH$_2$Cl$_2$ was added to a solution of 2.84 g (6.2 mmol) alcohol DA 59 in 14 mL CH$_2$Cl$_2$ at −78° C. The reaction mixture was allowed to warm up to 0° C. over a period of 2 h, quenched with 25 mL of NaHCO$_3$ saturated solution and diluted with 20 mL of diethyl ether. The organic phase was dried over anhydrous sodium sulfate and purified on preparative TLC using Hexane/Ethyl Acetate 98:2 to give 1.8 g (4 mmol; 64.5%) of a yellow oil. Rf=0.43 (Hex./AcOEt 97:3).

MS (IS): [M+Na]$^+$=483.1; 485.1; 487.1 (1:2:1) $^1$H-NMR (300 MHz, CDCl$_3$, δ): 0.2 (s, 6H, 2×CH$_3$), 1.0 (s, 9H, tBu), 3.8 (s, 3H, OCH$_3$), 5.6 (dd, 1H, CH, 3JHF=10 Hz, 2JHF=44 Hz), 6.8-6.9 (d, 1H, CH$_{ar}$), 7.0-7.1 (t, 2H, 2×CH). $^{13}$C-NMR (75 MHz, CDCl$_3$, δ): −4.4; 18.6; 25.9; 55.7; 96; 82.5; 82.8; 95.8; 96.1; 98.3; 98.7; 111.5; 121.1; 121.2; 122.4; 122.5; 124.4; 144.9; 152.8.

Synthesis of 1-bromo-1,2-difluoro-2-(4-methoxy-3-tert-butyl-dimethyl-syliloxyphenyl)ethene (4)

Step 1. Preparation of the tetramethylpiperidide solution. 1.9 mL (11.7 mmol; 3 eq.) of 2,2,6,6-tetramethylpiperidine was dissolved in 4 mL of anhydrous THF; the solution was cooled to −80° C. and then 3.9 mL (9.8 mmol; 2.5 eq) of a 2.5 M solution BuLi in Hexane were added. The mixture was stirred for 2 h at 0° C.

Step 2. Dehydrobromination. A solution of 1.8 g (3.9 mmol) of DA 62 in 5 mL of anhydrous THF was added to the tetramethyl piperidide solution previously cooled down to −100° C. After 1 h the reaction was washed with 10 mL HCl 0.1 N, the aqueous phase was back-extracted with 2×10 mL Et$_2$O. The organic extracts were collected and dried over anhydrous sodium sulfate and then purified on preparative silica plates with n-Hexane/Ethyl acetate 97:3 to give 857 mg (2.3 mmol; 59%) of product. Rf=0.8 in Hex./Acetone 8:2.

MS (IS): [M+Na]$^+$=401.4; 403.4 (1:1) $^1$H-NMR (300 MHz, CDCl$_3$, δ): 0.2 (s, 6H, 2×CH$_3$), 1.0 (s, 9H, tBu), 3.8 (s, 3H, OCH$_3$), 6.8-6.9 (d, 1H, CH), 7.1-7.15 (d, 1H, CH), 7.2-7.3 (dd, 1H, CH). $^{13}$C-NMR (75 MHz, CDCl$_3$, δ): -4;4; 18.6; 25.9; 55.7; 111.7; 120.5; 121.9; 122.0; 122.1; 124.3; 144.7; 151.9.

Synthesis of (Z)-1,2-difluoro-1-(3,4,5-trimethoxyphenyl)-2-(4-methoxy-3-tert-butyl-dimethyl-syliloxyphenyl)ethene (5)

A mixture of 750 mg (1.98 mmol; 1 eq.) of DA 63, 1.260 g (5.94 mmol; 3 eq.) of 3,4,5-trimethoxyphenyl-boronic acid, 4 mL of Na$_2$CO$_3$ 2M aqueous solution and 104 mg (0.09 mmol; 0.05 eq.) of Pd(Ph$_3$P)$_4$ in 20 mL toluene was refluxed overnight. The solution was then cooled down to room temperature, dried over anhydrous sodium sulfate and the crude mixture was passed through a short silica gel column to remove catalyst. The crude product was purified by chromatography on silica gel plates with Hexane/Acetone 8:2 to give 740 mg (1.6 mmol; 81%) of an oil. Rf=0.36 in Hex./Acetone 8:2.

MS (IS): [M+NH$_4$]$^+$=484.1; [2M+NH$_4$]$^+$=950.1 $^1$H-NMR (300 MHz, CDCl$_3$, δ): 0.5 (s, 6H, 2×CH$_3$), 1.0 (s, 9H, tBu), 3.65 (s, 6H, 2×OCH$_3$), 3.8 (s, 3H, OCH$_3$), 3.9 (s, 3H, OCH$_3$), 6.5-6.7 (t, 2H, 2×CH), 6.75-7.0 (dq, 3H, 3×CH). $^{13}$C-NMR (75 MHz, CDCl$_3$, δ): -4.6;1; 18.6; 25.8; 25.9; 55.7; 56.2; 56.3; 56.4; 61.0; 61.1; 103.4; 105.5; 111.9; 121.0; 122.5; 122.6; 123.8; 145.1; 153.3; 153.8.

Synthesis of (Z)-1,2-difluoro-1-(3,4,5 trimethoxyphenyl)-2-(3-hydroxy-4-methoxyphenyl)ethene (ST2303)

A 1M solution of Tetrabutylammonium fluoride in THF (9.4 mmol; 2 eq.) was dropped, at 0° C. and under inert atmosphere, to a solution of 2.2 g (4.7 mmol) of stilbene DA 64 in 10 mL of anhydrous THF (stored on molecular sieves). The reaction mixture was allowed to warm up to room temperature and after 4 h the reaction was complete. The mixture was poured into ice and the aqueous phase extracted with Et$_2$O (3×20 mL); the organic extracts were collected and dried over anhydrous Na$_2$SO$_4$.

The crude mixture was purified by chromatography on silica gel with n-Hexane/Acetone 8:2 to give 1.361 g (3.9 mmol; 83%).

M.p.=135° C.

MS (IS): [M+H]$^+$=353.0

[M+NH$_4$]$^+$=370.0

[M+Na]$^+$=375.0

[M-1]$^-$=351.0

$^1$H NMR (300 MHz, CDCl$_3$, δ): 3.75 (s, 6H, 2×OCH$_3$), 3.8 (s, 3H, OCH$_3$), 3.9 (s, 3H, OCH$_3$), 5.6 (broad, 1H, OH), 6.6 (s, 2H, 2×CH), 6.75-6.8 (d, 1H, CH), 6.85-6.9 (dd, 1H, CH), 7.0 (dd, 1H, CH). $^{13}$C NMR (75 MHz, CDCl$_3$, δ): 56.2; 61.1; 105.3; 105.4; 110.4; 114.5; 114.6; 121.1; 123.1; 123.6; 125.1; 125.6; 142.1; 145.6; 147.3; 147.5; 147.6; 153.1. $^{19}$F NMR (282 MHz, CDCl$_3$, δ): −126.2 (d, J$_{FF}$=14.8 Hz), −130.3 (d, J$_{FF}$=14.8 Hz).

EXAMPLE 2

Figure 2:
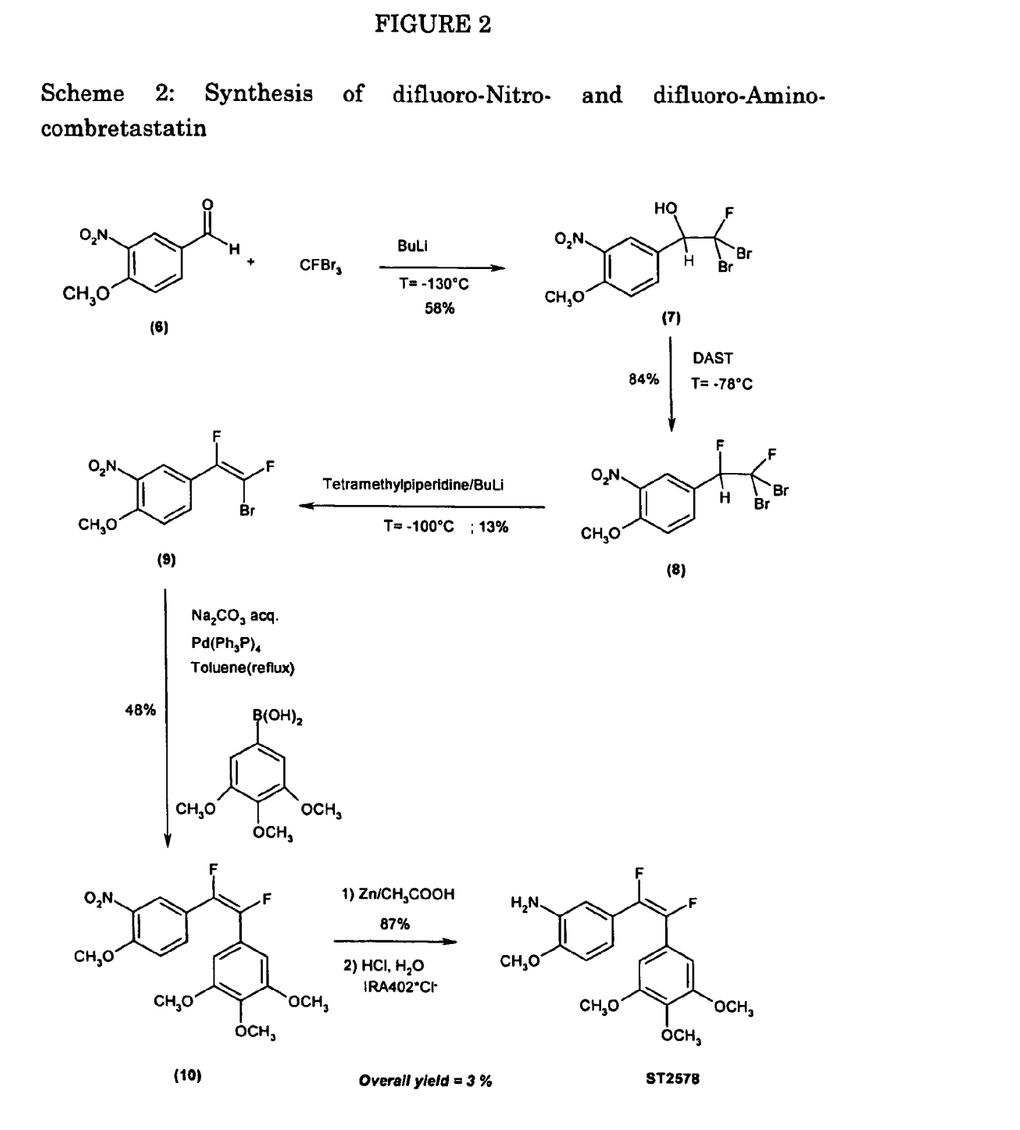
FIG. 2: synthesis of difluoronitro- and difluoroamino-combretastatin.

Synthesis of difluoronitro- and difluoroaminocombretastatin (Scheme 2)

Synthesis of 2,2-dibromo-2-fluoro-1-(3-nitro-4-methoxy-phenyl)ethanol (7)

A mixture of 978 mg (5.4 mmol) of 3-nitro-4-methoxy-benzaldehyde(6) and 1.6 g (5.9 mmol, 1.1 eq) of CFBr$_3$ in 40 mL of Et$_2$O/THF (1:1) was brought to T=−130° C.; 3.7 mL (5.9 mmol, 1.1 eq) of a 1.6 M BuLi solution in hexane was added to the mixture in 10 minutes.

The reaction was quenched with 25 mL of NH$_4$Cl saturated solution and diluted with 20 mL of diethyl ether. The aqueous phase was back-extracted with 2×20 mL of diethyl ether, the organic fractions were collected and dried over anhydrous sodium sulfate and then purified on a silica gel column using Hexane/EthylAcetate 95:5 to give 1.146 g (3.1 mmol, 57.4%) of a yellow oil. R$_f$=0.53 (Hex./AcOEt 6:4).

MS (IS): [M−1]$^-$=371.8

[M+AcO]$^-$=431.7

$^1$H-NMR (300 MHz, CDCl$_3$, δ): 3.2 (bs, 1H, OH), 4.0 (s, 3H, OCH$_3$), 5.1-5.2 (m, 1H, CH), 7.05-7.15 (d, 1H, CH$_{ar}$) 7.7-7.8 (d, 1H, CH$_{ar}$), 8.05 (s, 1H, CH$_{ar}$). $^{13}$C-NMR (75 MHz, CDCl$_3$, δ): 56.9; 81.5; 81.8; 98.9; 100.3; 104.6; 113.3; 126.3; 127.3; 134.3; 153.8.

Synthesis of 1,1-dibromo-1,2-difluoro-2-(3-nitro-4-methoxy-phenyl)ethane (8)

(DAST 730 μL (5.58 mmol; 1.8 eq) in 5 mL CH$_2$Cl$_2$ was added to a solution of 1.146 g (3.1 mmol) of the alcohol (7) in 7 mL CH$_2$Cl$_2$ at −78° C. The reaction mixture was allowed to warm up to 0° C. over a period of 2 h, quenched with 15 mL of NaHCO$_3$ saturated solution and diluted with 20 mL of diethyl ether. The organic phase was dried over anhydrous sodium sulfate and purified by chromatography on SiO$_2$ using Hexane/EthylAcetate 7:3 to give 960 mg (2.6 mmol; 84%) of a yellow oil. R$_f$=0.493 (Hex./AcOEt 7:3)

$^1$H-NMR (300 MHz, CDCl$_3$, δ): 4.0 (s, 3H, OCH$_3$), 5.55-5.80 (dd, 1H, CH,), 7.1-7.2 (d, 1H, CH$_{ar}$), 7.7-7.8 (d, 1H, CH$_{ar}$), 8.1 (s, 1H, CH$_{ar}$).

$^{13}$C-NMR (75 MHz, CDCl$_3$, δ): 29.9; 56.9; 94.4; 94.8; 97.0; 97.2; 97.4; 113.6; 124.1; 124.4; 126.2; 134.0; 139.4; 154.5.

Synthesis of (E)-1-bromo-1,2-difluoro-2-(3-nitro-4-methoxy-phenyl)ethene (9)

Step 1 Preparation of the Tetramethyl-piperidide solution. 1.3 mL (7.8 mmol; 3 eq.) of 2,2,6,6-tetramethyl-piperidine was dissolved in 3 mL of anhydrous THF.; the solution was cooled to −80° C. and then 3.9 mL (9.8 mmol; 2.5 eq) of a 2.5 M solution BuLi in Hexane were added. The mixture was stirred for 2 h at 0° C.

Step 2 Dehydrobromination. A solution of 960 mg (2.6 mmol) of (8) in 5 mL of anhydrous THF was added to the tetramethyl piperidide solution previously cooled down to −100° C. After 1 h the reaction was washed with 10 mL HCl 0.1 N, the aqueous phase was back-extracted with 2×10 mL Et$_2$O. The organic extracts were collected and dried over anhydrous sodium sulfate and then purified on silica gel with n-Hexane/Ethyl acetate 8:2 to give 100 mg (0.34 mmol; 13%) of product. $R_f$=0.36 in Hex./Acetone 8:2.

$^1$H-NMR (300 MHz, CDCl$_3$, δ): 4.0 (s, 3H, OCH$_3$), 7.1-7.2 (d, 1H, CH$_{ar}$), 7.8-7.9 (d, 1H, CH$_{ar}$), 8.2 (s, 1H, CH$_{ar}$). $^{13}$C-NMR (75 MHz, CDCl$_3$, δ): 57.0; 113.6; 113.8; 120.5; 120.9; 124.6; 125.1; 125.4; 126.2; 126.3; 128.8; 129.3; 133.3; 134.0; 141.1; 141.3; 144.4; 144.6; 154.0.

Synthesis of (Z)-1,2-difluoro-1-(3,4,5-trimethoxyphenyl)-2-(3-nitro-4-methoxy-phenyl)ethene (10)

A mixture of 90 mg (0.31 mmol; 1 eq.) of (9), 198 mg (0.93 mmol; 3 eq.) of 3,4,5-trimethoxyphenyl-boronic acid, 0.6 mL of Na$_2$CO$_3$ 2M aqueous solution and 19 mg (0.0016 mmol; 0.05 eq.) of Pd(Ph$_3$P)$_4$ in 4 mL toluene was refluxed for 2.5 h. The solution was then cooled down to room temperature, dried over anhydrous sodium sulfate and the crude mixture was passed through a short silica gel column to remove catalyst. The crude product was purified by chromatography on silica gel with Hexane/Acetone 8:2 to give 57 mg (0.15 mmol; 48%) of a yellow oil. $R_f$=0.17 in Hex./Acetone 8:2.

MS (IS): [M+H]$^+$=382.4; [M+NH$_4$]$^+$=399.3. $^1$H-NMR (300 MHz, CDCl$_3$, δ): 3.75 (s, 6H, 2×OCH$_3$), 3.85 (s, 3H, OCH$_3$), 4.0 (s, 3H, OCH$_3$), 6.6 (s, 2H, 2×CH$_{ar}$), 6.95-7.05 (dq, 1H, CH$_{ar}$), 7.4-7.5 (d, 1H, CH$_{ar}$), 7.9 (s, 1H, CH$_{ar}$).

$^{13}$C-NMR (75 MHz, CDCl$_3$, δ): 29.9; 56.4; 56.9; 61.2; 105.9; 113.6; 125.1; 133.3; 153.7.

Synthesis of (Z)-1,2-difluoro-1-(3,4,5-trimethoxyphenyl)-2-(3-amino-4-methoxyphenyl)ethene (ST2578)

To a solution of 40 mg (0.105 mmol) of nitro-stilbene (10) in AcOH (5 mL) was added zinc powder 75 mg (1.15 mmol; 11 eq.); the mixture was stirred at room temperature for 1.5 h. The reaction mixture was filtered over Celite and the filtrate evaporated to dryness.

The crude product was purified by chromatography on silica gel with CH$_2$Cl$_2$, then on preparative HPLC to give 32 mg (0.091 mmol; 87%) of a white solid. $R_f$=0.31 in CH$_2$Cl$_2$.

A small portion (4 mg) of the trifluoroacetate salt obtained from the prep. HPLC was passed through an ion-exchange column IRA402*Cl$^-$ to give 3 mg of the corresponding HCl salt (ST2578).

MS (IS): [M+H]$^+$=352.3; [2M+H]$^+$=703.1. $^1$H-NMR (300 MHz, CDCl$_3$, δ): 3.7 (s, 6H, 2×OCH$_3$), 3.85 (s, 3H, OCH$_3$), 4.0 (s, 3H, OCH$_3$), 6.6 (s, 2H, 2×CH$_{ar}$), 6.7-6.8 (t, 1H, CH$_{ar}$), 6.85-6.90 (d, 1H, CH$_{ar}$), 6.95 (s, 1H, CH$_{ar}$).

$^{13}$C-NMR (75 MHz, CDCl$_3$, δ): 29.9; 55.9; 56.3; 56.5; 61.1; 105.0; 105.4; 110.5; 116.6; 121.6; 122.8; 123.1; 125.5; 125.9; 133.0; 143.1; 143.9; 146.6; 149.5; 153.3; 153.7.

EXAMPLE 3

Figure 3:
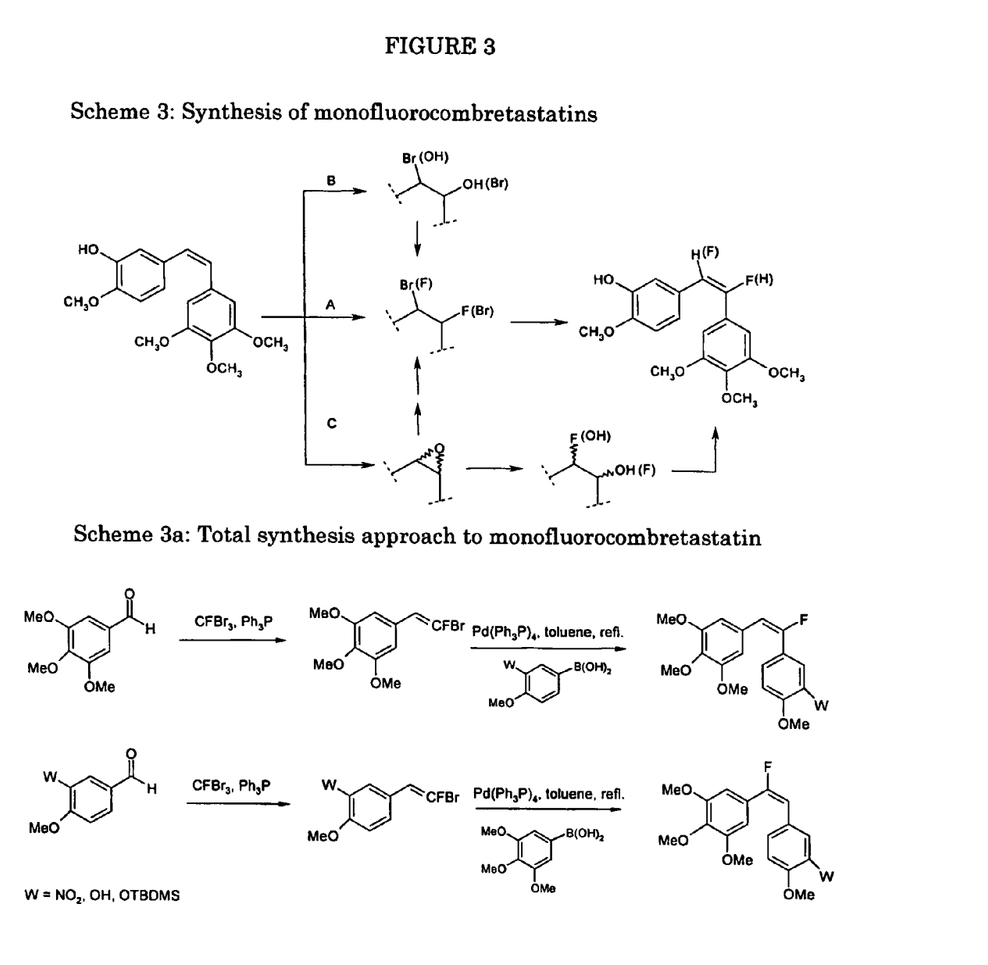
FIG. 3: synthesis of monofluorocombretastatin.

Synthesis of monofluorocombretastatins (Scheme 3)

Convenient approaches to the synthesis of both of the regioisomeric monofluorocombretastatins, starting from the natural CA-4, are the following:

A) Bromofluorination of the CA-4, followed by base-promoted HBr elimination (Giannini, G., *Gazz. Chim. It.*, 1997, 127, 545; Thakker D. R., et al., *J. Org. Chem.*, 1989, 54, 3091).

B) Fluorination, by DAST, of the bromohydrin obtained from the CA-4, followed by base-promoted HBr elimination.

C) Synthesis of the epoxide from the CA-4, epoxide opening to obtain:

the bromohydrin and to continue as point B), or the fluorohydrin followed by elimination of opportune hydroxyl derivative.

Alternatively, the monofluorocombretastatins can be obtained by total synthesis according to Scheme 3a Key intermediates for this approach can be prepared as exemplified below for the 3,4,5-trimethoxybenzaldheyde.

Synthesis of (E/Z)-1-fluoro-2-(3,4,5-trimethoxyphenyl)ethene 1.63 g (6 mmol, 1.2 eq,) of CFBr$_3$ have been added to a solution of 2.9 g (11 mmol, 2.2 eq.) of Ph$_3$P in 30 mL CH$_2$Cl$_2$ kept in an ice bath. After 30 minutes at this temperature, 980 mg of 3,4,5-trimethoxybenzaldheyde have been added to the mixture and the reaction has been allowed to warm up to room temperature over 2 hours. The mixture has been diluted with 50 mL CH$_2$Cl$_2$ and washed with brine. The crude product has purified by silica gel chromatography with Hexane(EtOAc 9:1 to give 758 mg (2.6 mmol; 52%) of a 53:47 Z/E mixture of the desired product as a colourless oil. Rf=0.23 in Hex/EtOAc 9:1.

MS (IS): [M+H]$^+$=291.0/293.0

(Z)-Isomer (obtained by preparative HPLC) $^1$H-NMR (200 MHz, CDCl$_3$, δ): 3.88 (s, 3H, OCH$_3$), 3.89 (s, 6H, 2×OCH$_3$), 6.66 (d, J=15.4 Hz, 1H, CH), 6.75 (s, 2H, 2×CH$_{ar}$). (E)-Isomer (obtained by preparative HPLC) $^1$H-NMR (200 MHz, CDCl$_3$, δ): 3.87 (s, 9H, 3×OCH$_3$), 5.93 (d, J=32.2 Hz, 1H, CH), 6.65 (s, 2H, 2×CH$_{ar}$).

This intermediates can undergo a classical Suzuki-like coupling with the proper boronic acid. (see Scheme 3a)

EXAMPLE 4

Figure 4:
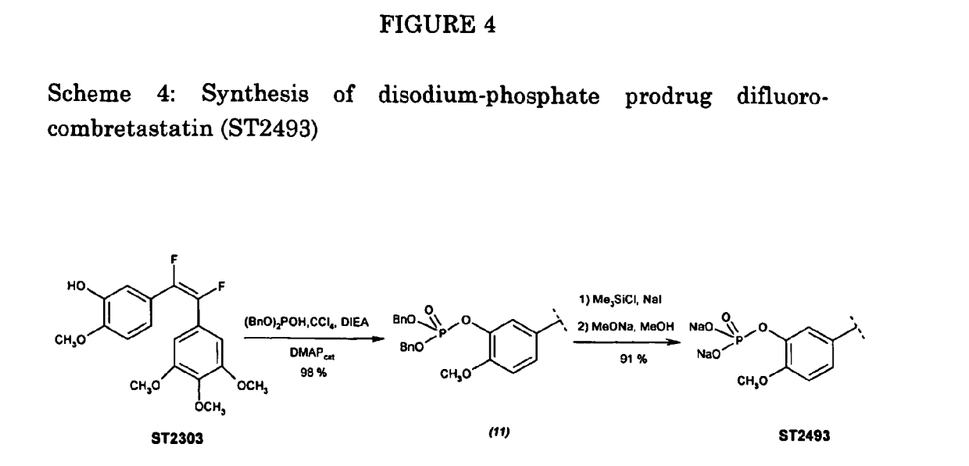
FIG. 4: synthesis of difluorocombretastatin disodium-phosphate.

Synthesis of Disodium-Phosphate Prodrug of Difluorocombretastatin (Scheme 4)

A typical procedure for the synthesis of the disodium-phosphate prodrug is well known in the literature (Pettit, G. R., et al., *Anti-Cancer Drug Design* 1998, 13, 183-191) and is intended to be generally applicable to all the compounds here described, possessing a free phenolic moiety. As an example, the synthesis of the disodium-phosphate prodrug of compound (6) is here reported.

Synthesis of (Z)-1,2-difluoro-1-(3,4,5-trimethoxyphenyl)-2-(3-hydroxy-4-methoxyphenyl)ethene o-dibenzyl-phosphate (11)

To a solution of 30 mg of (6) (0.09 mmol) in 1 mL dry CH$_3$CN, cooled down to −25° C., 44 μL (0.45 mmol; 5 eq.) CCl$_4$ were added. After 5 minutes mixing 33 μL (0.19 mmol; 2.1 eq.) diisopropyl-ethyl amine, 1 mg (0.009; 0.1 eq.) DMAP and 29 μL of di-benzyl phosphite were added to the solution and the reaction mixture was stirred for 1.5 h at −10° C.

The reaction was quenched by pouring 5 mL KH$_2$PO$_4$ 0.5 M; the aqueous phase was washed with AcOEt (3×10 mL) and the organic phase was back-extracted with 10 mL H$_2$O and then with 10 mL NaCl saturated solution. The crude mixture was purified by silica gel chromatography with Hexane/AcOEt 6:4 to give 55 mg of a colourless oil (0.088; 98%). $R_f$=0.32 in Hex./AcOEt 6:4

MS (IS): [M+H]$^+$=613.4; [M+NH$_4$]$^+$=630.2; [M+Na]$^+$=635.0. $^1$H-NMR (300 MHz, CDCl$_3$, δ): 3.70 (s, 6H, 2×OCH$_3$); 3.80 (s, 3H, OCH$_3$); 3.85 (s, 3H, OCH$_3$); 5.65 (s,

2H, CH$_2$); 5.70 (s, 2H, CH$_2$); 6.55 (s, 2H, 2×CHar.); 6.80-6.85 (d, 1H, CHar.); 7.10-7.15 (dd, 1H, CHar.); 7.25 (s, 1H, CHar.); 7.35-7.45 (m, 10H, CHar.). $^{13}$C-NMR (75 MHz, CDCl$_3$, δ): 29.6; 29.9; 56.1; 56.3; 56.4; 61.1; 70.1; 70.3; 104.3; 105.4; 106.4; 109.1; 112.6; 115.1; 121.7; 125.0; 126.6; 128.1; 128.2; 128.8; 128.9; 129.2; 130.9; 132.3; 135.7; 145.5; 153.2; 153.4.

Synthesis of (Z)-1,2-difluoro-1-(3,4,5-trimethoxyphenyl)-2-(3-hydroxy-4-methoxyphenyl)ethene o-disodium phosphate [ST2493]

To a solution of 50 mg (0.08 mmol) of (11) in 1.5 mL dry CH$_3$CN in a three-necked round-bottom flask and under an Ar atmosphere, 24 mg (0.16 mmol; 2 eq.) of NaI were added. The mixture was stirred at room temperature for 10 minutes and then a solution of 20 μL (CH$_3$)$_3$SiCl (0.16 mmol; 2eq.) in 1 mL CH$_3$CN was dropped in.

After 1.5 h one equivalent of NaI and one equivalent of (CH$_3$)$_3$SiCl were added to complete the reaction. Water (just enough to dissolve the salts) was added and the pale yellow colour removed by the addition of 10% aq. Na$_2$S$_2$O$_3$ (1 mL). The organic phase was separated and the aqueous phase extracted with AcOEt (4×4 mL). The combined organic extracts were concentrated to give a yellow waxy solid.

The solid was dissolved in 1.5 mL dry MeOH (stored on molecular sieves) and 9 mg (0.16 mmol; 2 eq.) of sodium methoxide were added and the solution stirred at room temperature for 12 h. The methanol was removed in vacuo and the solid recrystallized from water-acetone and methanol-acetone to give 35 mg (0.073 mmol; 91%) of compound (ST2493) as a white solid.

$^1$H-NMR (200 MHz, D$_2$O, δ): 3.60 (s, 6H, 2×OCH$_3$); 2.70 (s, 3H, OCH$_3$); 3.8 (s, 3H, OCH$_3$); 6.70 (bs, 2H, 2×CHar.); 6.85 (bs, 2H, 2×CHar.); 7.55 (s, 1H, CHar.).

EXAMPLE 5

Figure 5:
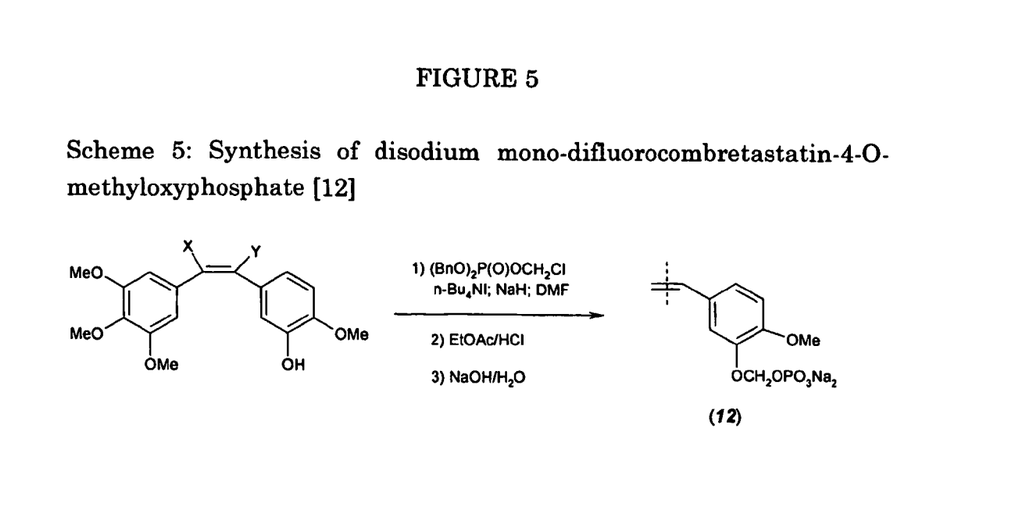
FIG. 5: synthesis of mono-difluorocombretastatin disodium-oxymetil-phosphate.

Synthesis of disodium mono difluorocombretastatin-4-O-methyloxyphosphate [12]

The prodrug 12 were prepared by the route described in Scheme 5.

Typical methyloxy-phosphorylation method was first treated the phenolic residue with sodium hydride followed by protected chloromethyl phosphate prepared as a described method [Mantyla A. et al. *Tetrahedron Lett.* 2002, 43, 3793-4). The protecting group was removal by a saturated EtOAc/HCl solution, followed by a disodium salt preparation in NaOH/H$_2$O solution.

EXAMPLE 6

Figure 6:
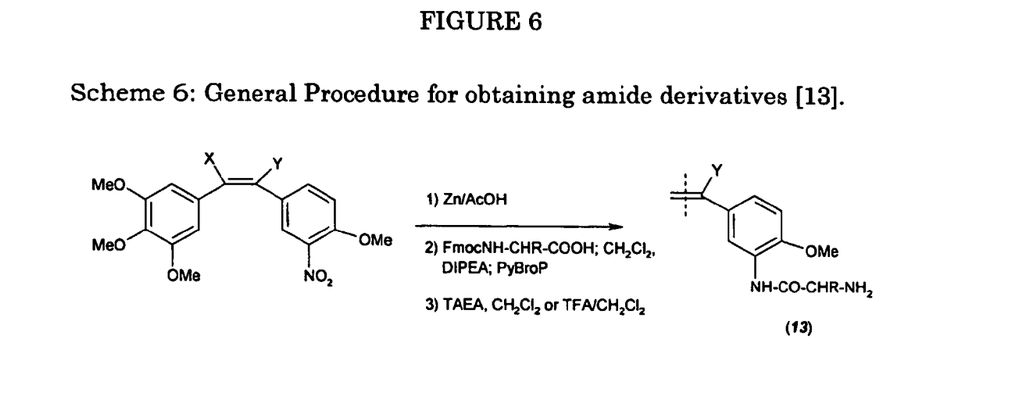
FIG. 6: synthesis of mono-difluoroaminocombretastatin aminoacid amide derivatives.

Synthesis of mono-difluoroaminocombretastatin aminoacid amide derivatives [13]

Starting with aminostilbene derivatives, the coupling with aminoacids has been produced by Fmoc route, followed by cleavage of the α-amino protecting group [G. R. Pettit et al., *J. Med. Chem* 2002, 46, 525-31], according to Scheme 6.

EXAMPLE 7

Synthesis of bromofluoroaminocombretastatin [14]

According to procedure in Scheme 7, have been isolated, after flash chromatographic separation, the two isomers (E and Z) of the bromofluorocombretastatin.

Cell Culture and Cytotoxicity Assay

Primary cultures of bovine microvascular endothelial cells (BMEC) were obtained from bovine adrenal glands as described by Folkman (Folkman J., Haudenschild C. C., Zetter B. R. *Long-term culture of capillary endothelial cells. Proc. Natl. Acad. Sci. USA,* 1979 October; 76(10): 5217-21). BMEC were maintained in DMEM supplemented with 20% fetal calf serum (FCS), 50 units/ml heparin (Sigma, St. Louis, Mo.), 50 μg/ml bovine brain extract, 100 units/ml gentamycin. HUVEC (Human umbilical vein endothelial cells) were obtained from BioWhittaker (Walkersville, Md.) and grown in EGM-2 (BioWhittaker). EA-hy 926 cell line, a HUVEC-adenocarcinoma immortalized cell hybrid, was obtained from the Dipartimento di Scienze Biomediche e Oncologia Umana (Universita di Bari, Italy), and cultured in DMEM supplemented with 10% serum and 50 μg/ml gentamycin sulfate.

The following cell lines were purchased from ATCC and cultured according to manufacturer's instructions: NCIH460 human lung carcinoma, MeWo human melanoma, MES-SA human uterine sarcoma and HCT116 human colorectal carcinoma. HT-29 human colon adenocarcinoma cells and A2780 human ovarian carcinoma, obtained from Istituto Nazionale Tumori (Milan, Italy), were grown in RPMI 1640 (GIBCO) containing 10% fetal bovine serum (GIBCO) and 50 μg/ml gentamycin sulfate.

To test the effects of ST2303 on growth, cells were seeded in 96-well tissue culture plates (Corning) at approximately 10% confluence and were allowed to attach and recover for at least 24 h. Varying concentrations of the compound were then added to each well. The plates were incubated for 24 h and then washed before incubating them for additional 48 h. The number of surviving cells was then determined by staining with sulforhodamine B as described by Skehan et al. (1990). ST2303 inhibitory concentration 50 (IC$_{50}$)±SD on different cell lines, evaluated by "ALLFIT" computer program, are shown in Table 1.

TABLE 1

| | (ST2303) |
|---|---|
| Cell line | IC$_{50}$ ± SE (nM) |
| BMEC | 1 ± 0.5 |
| HUVEC | 1 ± 0.3 |
| EAHY.926 | 5 ± 0.5 |
| NCI-H460 | 3 ± 0.005 |
| HT29 | >200 |
| MeWo | 3.6 ± 0.0003 |
| A2780 | 3 ± 0.001 |
| MES-SA | <1 |
| HCT 116 | 2.2 ± 0.05 |

Tumor Growth Evaluation

NCI-H460 human lung carcinoma from in vitro cell cultures were injected s.c. (3×10$^6$ cells/100 μl/mouse) into the right flank of CD-1 nude mice. Four days after tumor implant mice started to be treated with ST2493 at the dose of 50 mg/kg intraperitoneally according to the following schedule: qdx5/w/3wks. CA-4P (combretastatin A-4 P) at the same dose was used as positive control.

All animals were weighed during the whole treatment period, in order to adjust the volume of drug administration and to record the percent of body weight loss due in the course of treatment.

In a following experiment with the same animal model ST2493 (prodrug of ST2303) was administered intravenously at the doses of 25 and 50 mg/kg according to a q2dx6 schedule.

Tumor growth was assessed by twice a week measurements of the shortest (width) and the longest (length) diameters of each tumor by a Vernier caliper and the antitumor activity was evaluated in terms of percent inhibition of tumor growth. Tumor volume (or tumor weight*) was calculated according to the following formula using caliper measurements: tumor volume or TV (mm$^3$)=[length (mm)×width (mm)$^2$]/2.

Tumor volume inhibition percent (% TVI) was calculated according to the equation: 100−[(mean tumor volume of treated group/mean tumor volume of control group)×100]. A P value≦0.05 was considered statistically significant.

Results, reported in Table 2, show that both intraperitoneal and intravenous administration of ST2493 determined a significant TVI compared to vehicle. In the intraperitoneal treatment the comparison of ST2493 with the same dose of CA-4P demonstrated a significant difference between the two compounds (p=0.0095 at day 11 and p=0.0180 at day 28, Mann Whitney's test).

TABLE 2

| Treatment | n | % BWL | mortality | % TVI Days after cell injection 11 | 28 |
|---|---|---|---|---|---|
| Vehicle (saline) | 8 | 0 | 0/8 | / | / |
| ST2493 i.p. 50 mg/kg | 8 | 8 | 0/8 | 68** | 73*** |
| CA-4P i.p. 50 mg/kg | 8 | 3 | 0/8 | 47** | 61*** |
| ST2493 i.v. 25 mg/kg | 8 | 8 | 0/8 | 63** | 64*** |
| ST2493 i.v. 50 mg/kg | 8 | 8 | 0/8 | 73** | 73** |

*P < 0.05,
**P < 0.01,
***P < 0.001 vs vehicle (Mann Whitney's test)

Tubulin Polymerisation Inhibition Test

The tubulin polymerisation test was performed by Cyto-DINAMIX Screen™. Turbidity from tubulin polimerisation was measured with a Victor2 from Wallac. HTS-tubulin was diluted to 3 mg/ml in buffer PEM [100 mM PIPES (pH 6.9), 1 mM EGTA and 1 mM MgCl$_2$] containing 1 mM GTP (GPEM) plus 5% glycerol, and kept on ice. Aliquots of this solution was then placed at 37° C. in presence of taxol (3 μM) or colcemid (3 μM) or combretastatin (ST1986) or compounds to examinate, and absorbance was measured at 340 nm. The IC$_{50}$ values were determined by non-linear regression analysis using "Prism GraphPad" software.

The value indicated in Table 3 is the mean of 3 independent determinations.

TABLE 3

| Compound | IC50 ± SE (μM) |
|---|---|
| ST2303 | 7.7 ± 0.12 |
| ST1986 | 14.4 ± 5.8 |

The invention claimed is:

1. A compound of formula (I)

wherein:
R$_1$, R$_2$ and R$_3$, which can be the same or different, are OMe, NO$_2$, NHR';
X and Y, are halogen or H with at least one of them being halogen;
Z=H or halogen
R=OH, OPO$_3$Na$_2$, OCH$_2$OPO$_3$Na$_2$, NO$_2$, NHR';
R'=H, alkyl (C$_1$-C$_6$);
its pharmaceutically acceptable salts, racemate and single enantiomers.

2. A compound according to claim 1, selected from the group consisting of:
a compound wherein at least one of X and Y is halogen, R$_1$-R$_3$ are methoxy, and R is hydroxy;
a compound wherein at least one of X and Y is halogen, R$_1$-R$_3$ are methoxy, R is amino or substituted amino;
a compound wherein at least one of X and Y is halogen, R$_1$-R$_3$ are different from methoxy, R is hydroxy; and
a compound wherein R is OPO$_3$Na$_2$.

3. A compound according to claim 1, wherein R" is the side chain of a natural amino acid.

4. A compound according to claim 1 selected from the group consisting of:
X=Y=F; R=OPO$_3$Na$_2$: difluorocombretastatin;
X=Y=F; R=NH$_2$: difluoroaminocombretastatin;
X=H; Y=F; R=OPO$_3$Na$_2$: monofluorocombretastatin;
X=F; Y=H; R=OPO$_3$Na$_2$: monofluorocombretastatin;
X=H; Y=F; R=NH$_2$: monofluoroaminocombretastatin;
X=F; Y=H; R=NH$_2$: monofluoroaminocombretastatin.
X=Br; Y=F; R=OPO$_3$Na$_2$ bromofluorocombretastatin 5. A process for the preparation of the compounds of claim 1, wherein X and Y are both F comprising the following steps:
a) reaction of 1-bromo-1,2-difluoro-2-(4-methoxy-3-(protected OH)-phenyl)ethene with 3-R$_1$-4-R$_2$-5-R$_3$-phenylboronic acid, and
b) restoring the 3-(protected OH) group.

6. A process for the preparation of compounds of claim 1, wherein one of the X and Y is F and the other one is hydrogen, comprises the following steps:
a) bromofluorination of the compound of Formula (I), wherein X and Y are H, and
b) base-promoted HBr elimination.

7. A process for the preparation of compounds of claim 1, wherein one of the X and Y is F, comprising the following steps:
a) transformation of compound of Formula (I), wherein X and Y are H into the respective bromohydrin, and
b) base-promoted HBr elimination.

8. A process for the preparation of compounds of claim 1, wherein one of the X and Y is F, comprising the following steps:
a) transformation of compound of Formula (I), wherein X and Y are H into the respective epoxide;

b) epoxide opening to give the respective bromohydrin, and c) base-promoted HBr elimination, or in alternative, d) epoxide opening to give the respective fluorohydrin, and e) elimination of the opportune hydroxyl derivative.

9. A process for the preparation of compounds of claim 1, wherein one of the X or Y is F and the other is Br, comprising the following steps:

a) transformation of compound of Formula (I), wherein X and Y are H into the respective bromohydrin, and b) base-promoted HBr elimination.

10. A method of inhibiting tubulin polymerization comprising administering to a subject an effective amount of a compound of claim 1.

11. A method of treating a tumour selected from the group consisting of sarcoma, carcinoma, carcinoid, bone tumour, neuroendocrine tumour, lymphoid leukaemia, acute promyelocytic leukaemia, myeloid leukaemia, monocytic leukaemia, megakaryoblastic leukaemia, non Hodgkin's disease, hemangiomas and multiple myeloma, and anaplastic thyroid cancer, comprising administering to a subject an effective amount of a compound of claim 1.

12. A method of treating a pathological state caused by abnormal angiogenesis selected from the group consisting of tumour metastases; arthritic disease; diabetic retinopathy; macular degeneration, psoriasis; chronic inflammatory diseases and arteriosclerosis comprising administering to a subject an effective amount of a compound of claim 1.

13. A pharmaceutical composition comprising at least a compound of claim 1, in admixture with at least one pharmaceutically acceptable carrier and/or excipient.

14. A method of treating ischemia-induced proliferative retinopathy comprising administering to a subject an effective amount of a compound of claim 1.

15. A method of treating a lung carcinoma comprising administering to a subject an effective amount of a compound of claim 1.

* * * * *